US012186233B2

(12) United States Patent
Li et al.

(10) Patent No.: US 12,186,233 B2
(45) Date of Patent: Jan. 7, 2025

(54) NON-SLIP CONDOM

(71) Applicant: Guangzhou Wanfangjian Pharmaceutical Co., Ltd., Guangdong (CN)

(72) Inventors: Huazhi Li, Guangdong (CN); Yongling Yuan, Guangdong (CN); Zhijun Lu, Guangdong (CN)

(73) Assignee: Guangzhou Wanfangjian Pharmaceutical Co., Ltd., Guangzhou (CN)

( * ) Notice: Subject to any disclaimer, the term of this patent is extended or adjusted under 35 U.S.C. 154(b) by 659 days.

(21) Appl. No.: 17/606,046

(22) PCT Filed: Apr. 23, 2020

(86) PCT No.: PCT/CN2020/086511
§ 371 (c)(1),
(2) Date: Oct. 25, 2021

(87) PCT Pub. No.: WO2020/221107
PCT Pub. Date: Nov. 5, 2020

(65) Prior Publication Data
US 2022/0202608 A1 Jun. 30, 2022

(30) Foreign Application Priority Data
Apr. 30, 2019 (CN) .......................... 201910367395.1

(51) Int. Cl.
*A61F 6/04* (2006.01)
(52) U.S. Cl.
CPC .......... *A61F 6/04* (2013.01); *A61F 2006/048* (2013.01)

(58) Field of Classification Search
CPC ........ A61F 6/04; A61F 2006/048; A61F 5/41; A61F 2005/414; A61F 2006/041;
(Continued)

(56) References Cited

U.S. PATENT DOCUMENTS

| 6,135,112 | A | 10/2000 | Harrison et al. |
| 2013/0133665 | A1* | 5/2013 | Waller ...................... A61F 6/06 2/400 |

FOREIGN PATENT DOCUMENTS

| CN | 201171738 Y | 12/2008 |
| CN | 201743815 U | 2/2011 |

(Continued)

OTHER PUBLICATIONS

International Search Report of PCT Patent Application No. PCT/CN2020/086511 issued on Jul. 21, 2020.

*Primary Examiner* — Ophelia A Hawthorne

(57) ABSTRACT

The present disclosure discloses a non-slip condom, including a sleeve body, where the sleeve body has an open end, a closed end, a male side, and a female side; no less than 5% of a bottom surface of the male side has a primary microstructure capable of increasing a surface area; and an area ratio of a total surface area per unit area of the bottom surface of the male side including the primary microstructure to the unit area is 1.05 to 565.00. The condom provided by the present disclosure can keep fit with a male penis during sexual intercourse to reduce the relative slip between the condom and the penis skin, and is not easy to wrinkle or slip off, thus reducing the mucosal injury and unreality sensation. Moreover, the condom helps to increase the consumers' willingness to use the condom and prevent sexually transmitted diseases (STDs).

22 Claims, 5 Drawing Sheets

(58) Field of Classification Search
CPC ............ A61F 6/005; A61F 6/146; A61F 6/00;
A61F 6/065; A61F 6/02; A61F 2005/411;
A61F 5/453; A61F 6/06; A61F 13/471;
A61F 5/40; Y10S 128/918
See application file for complete search history.

(56) References Cited

FOREIGN PATENT DOCUMENTS

| | | | |
|---|---|---|---|
| CN | 203493801 U | 3/2014 | |
| CN | 104127278 A | 11/2014 | |
| CN | 104394812 A | 3/2015 | |
| CN | 204446250 U | 7/2015 | |
| CN | 207286205 U | 5/2018 | |
| EP | 1003448 B1 | 10/2003 | |
| WO | 9534261 A1 | 12/1995 | |

\* cited by examiner

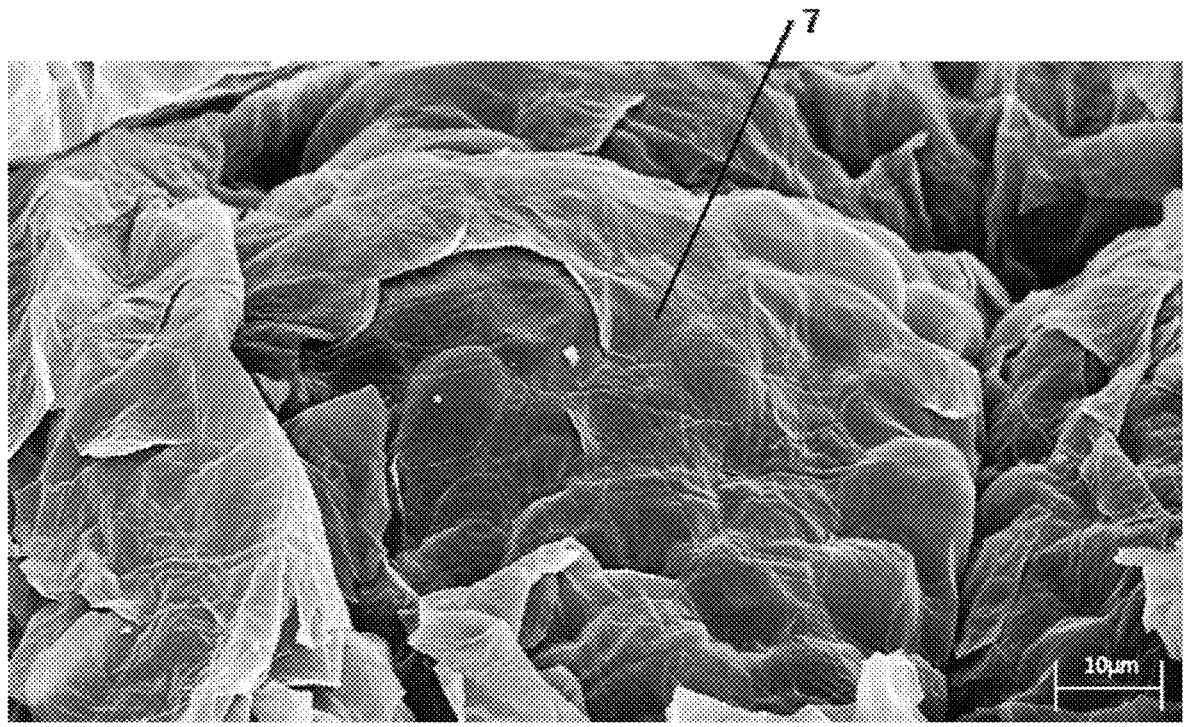
FIG. 3
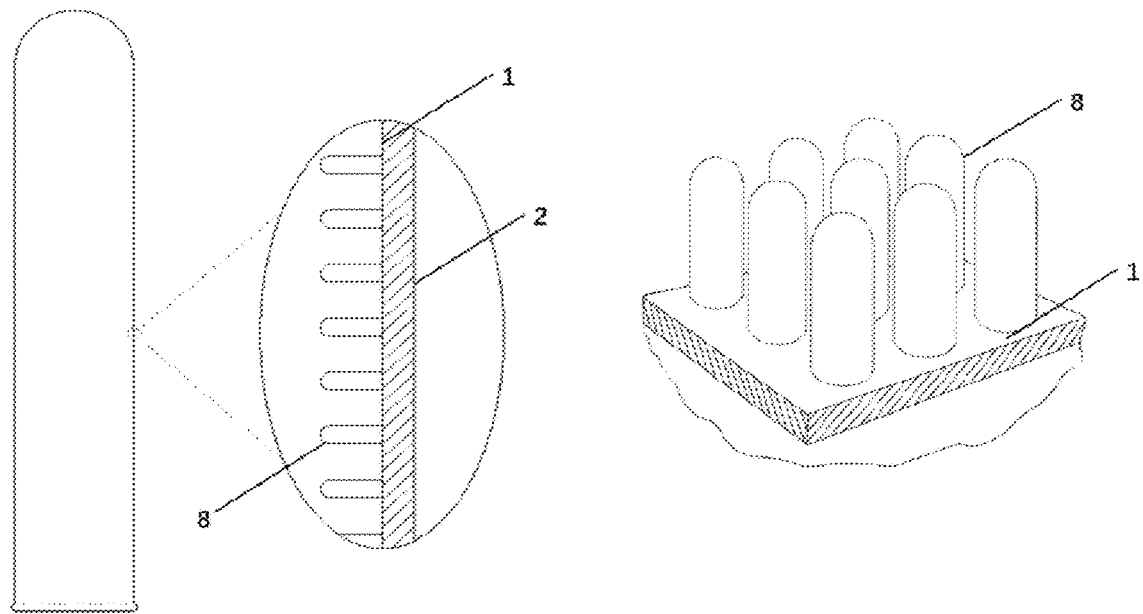
FIG. 4A
FIG. 4B

 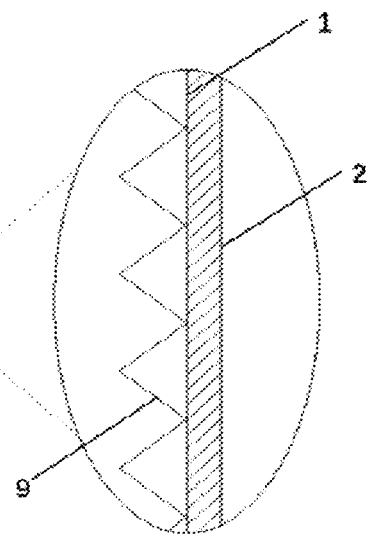 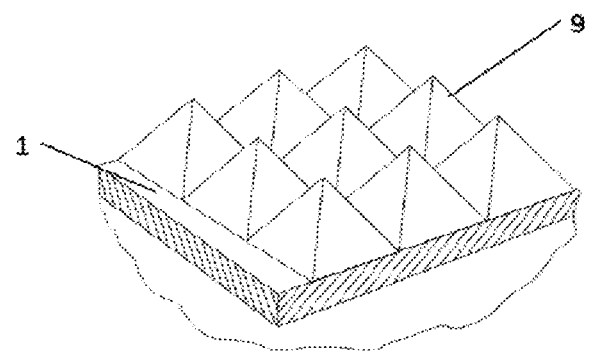
FIG. 5A  FIG. 5B
 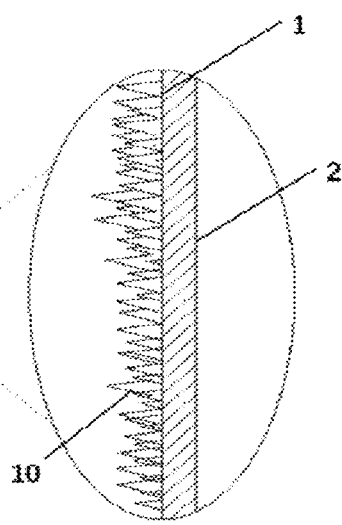 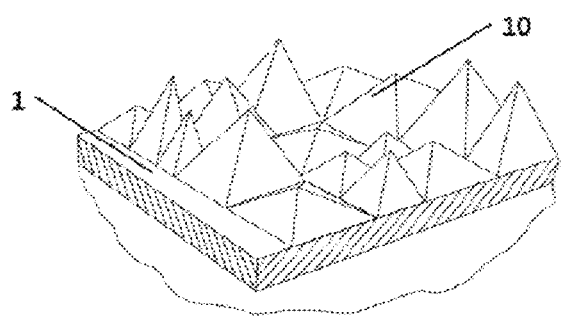
FIG. 6A  FIG. 6B

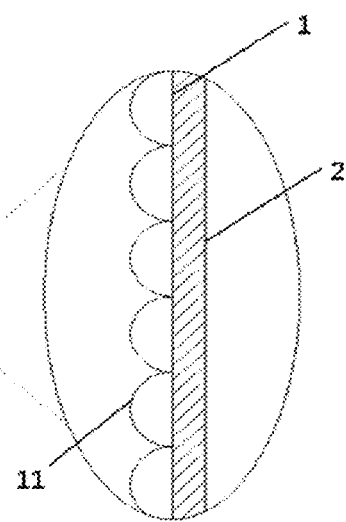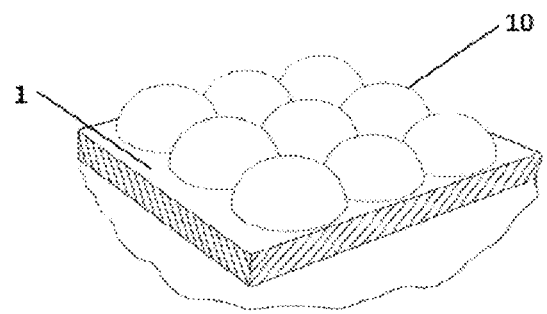
FIG. 7A                    FIG. 7B
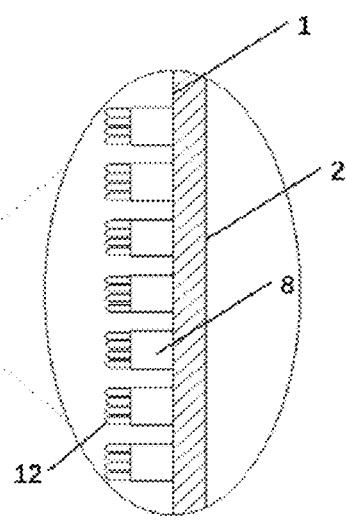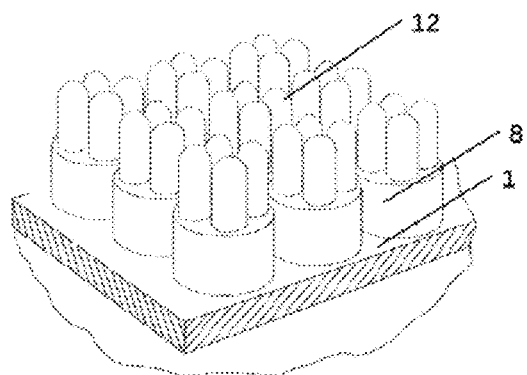
FIG. 8A                    FIG. 8B

NON-SLIP CONDOM

TECHNICAL FIELD

The present disclosure relates to the technical field of condoms, and in particular to a non-slip condom that can well fit the skin of a penis. The condom provided by the present disclosure can keep fit with a male penis during sexual intercourse to reduce the relative slip between the condom and the skin of the penis; the condom can be easily removed at the end of sexual intercourse; and the condom is not easy to wrinkle or slip off in use, which can reduce the mucosal injury and unreality sensation and helps to improve the consumers' sexual experience and the consumers' willingness to use the condom, thereby facilitating the prevention of various sexually transmitted diseases (STDs).

BACKGROUND

Condoms are widely used in human sexual life, and routine functions thereof include: prevention of pregnancy, and prevention of cross-infection of various sexually transmitted diseases (STDs), especially human immunodeficiency virus (HIV). When a condom is in use, an inner side of the condom in contact with a male penis is called a male side 1, and an outer side of the condom in contact with a canal (female vagina or anorectal colon) is called a female side 2; and an end receiving sperm is called a closed end 3, and a corresponding end is called an open end 4. A condom structure is shown in FIG. 1.

Data of a large survey shows that the utilization of condoms is not high enough. According to analysis, some people are unwilling to use a condom, because the condom does not fit closely to the skin of a male penis, and is easy to slip relatively, which sometimes causes the condom to wrinkle or even slip off, resulting in a series of problems. For example, wrinkles of a condom lead to unreality and foreign body sensation; friction between wrinkles and a mucous membrane can easily damage the mucous membrane, causing bleeding and/or painful intercourse; the slipping off of a condom leads to contraceptive failure and increased risk of pathogenic cross-infection; and in use, it is necessary to flatten a condom to remove large wrinkles, and a new condom needs to be used after the original condom slips off, resulting in temporary interruption of sexual intercourse. All these problems have severely affected the sexual experience of consumers, thereby reducing the willingness of a consumer to use a condom.

In order to overcome the above-mentioned problems of existing condoms, some attempts have been made by researchers in the art, including:

Chinese patent CN203493801U discloses a technical solution to make a condom well fit a penis by reducing a diameter of the condom. However, a reduced part of such a condom will still slip relative to a penis, and other parts that are not reduced will slip more easily; and the reduced part will compress blood vessels and nerves and cause difficulty in wearing. Therefore, this solution is not an ideal solution.

Chinese patent CN201743815U discloses a technical solution to symmetrically add raised particles at two sides of a condom, which aims to increase the stimulant effect of the condom on a male genitals during sexual intercourse and prevent the condom from slipping off. However, with the condom produced by this solution, particles at the male side will locally reduce a contact area between the condom and the penis skin and thus reduce a friction force, which cannot achieve the non-slip effect envisaged by the inventors.

U.S. Pat. No. 6,135,112 discloses a technical solution to arrange one or more rings at the open end of a condom near the ring and locally reduce a diameter of a sleeve body, aiming to provide a non-slip condom. However, when such a condom is used, the local reduced part will make a consumer feel very uncomfortable due to high tightness, and the added rings are not easy to wear and make it difficult to roll up the condom during production.

European Union patent EP1003448B1 discloses a technical solution to arrange an adhesive layer on an inner surface of a condom at 1/3 of a length from the open end, which aims to keep the condom fit and avoid slip during sexual intercourse. However, the adhesion of the adhesive layer to the penis skin will cause discomfort to a consumer, and the existence of the adhesive layer makes it impossible to add a lubricant to an inner surface of the condom, which increases the difficulty in use.

Patent WO95/34261 discloses a technical solution to add a specific material with a friction coefficient of more than 1.0 as an inner film at the male side of a condom, which aims to increase the friction at the male side of the condom and prevent the condom from slipping. However, the condom only wraps the skin of the erect penis, does not result in too much pressure and great friction, and thus fails to prevent slip. In addition, different inner film materials will affect the high memory elasticity and safety of the condom.

Although researchers in the art have tried the above-mentioned different technical solutions, actual application effects are unideal, and the problem that a condom slips on the penis skin, wrinkles, or even slips off in use is not solved. Therefore, there is an urgent need to develop a non-slip condom that can fit closely to the penis skin and is not easy to slip or slip off in use.

SUMMARY

Based on the above-mentioned problems, the present disclosure provides a non-slip condom that can overcome the shortcomings in the art, can fit closely to the penis skin, and is not easy to slip or slip off in use. The condom provided by the present disclosure can keep fit with a male penis in use to prevent the relative slip between the condom and the skin of the penis; the condom can be easily removed after use; and the condom is not easy to wrinkle or slip off in use, which can avoid the mucosal injury and reduce unreality sensation and helps to improve the consumers' sexual experience and the consumers' willingness to use the condom.

To achieve the above objective, the present disclosure adopts the following technical solutions:

The present disclosure provides a non-slip condom, comprising a sleeve body, where the sleeve body has an open end, a closed end, a male side, and a female side; no less than 5% of a bottom surface of the male side has a primary microstructure capable of increasing a surface area; and an area ratio of a surface area per unit area of the bottom surface of the male side comprising the primary microstructure to the unit area is 1.05 to 565.00. The bottom surface is an imaginary whole or local region of the male side with a smooth surface.

It should be noted that, under a microscope, on skin grooves 5 and skin bulges 6 on a surface of the penis skin, there are a large number of partially exfoliated keratinocytes, and many uneven microstructures 7 with sizes ranging from hundreds of nanometers to hundreds of micrometers (as shown in FIG. 2 to FIG. 3). The inventors of the present disclosure find in research that the larger the effective contact area between the condom and the penis skin during sexual intercourse, and the better the complementarity of the condom with the microstructures, the closer the fit between the condom and the penis skin, and the less likely the condom to slip.

When there is a primary microstructure at the male side of the condom, and a size and a shape of the primary microstructure enable the complementation of the primary microstructure with the various microstructures on the surface of the penis skin, the male side of the condom can well contact the various microstructures on the surface of the penis skin to increase an effective contact area between the male side of the condom and the penis skin, thereby achieving the purpose of close fit and non-slip. The larger the surface area of the primary microstructure, the more the increased surface area of the condom, the larger the area ratio, the better the complementarity between the male side of the sleeve body with the microstructure and the microstructure of the penis skin, and the larger the effective contact area.

Preferably, 20% to 95% of the bottom surface of the male side of the condom may have the primary microstructure capable of increasing a surface area. As a result, some regions at the male side of the condom are not provided with the primary microstructure, which helps the condom to be worn and removed from a softened penis; and a proportion of a part with the primary microstructure on the bottom surface of the male side of the condom can be adjusted to adapt to the physiological characteristics and different needs of different populations.

Preferably, the area ratio may be 1.1 to 100.0, and more preferably, the area ratio may be 1.2 to 50.0.

Preferably, different regions with the primary microstructure on a longitudinal axis and/or a horizontal axis of the male side may have the same average area ratio. The average area ratio refers to a ratio of a total surface area of the male side of a selected region including the primary microstructure to an area of the bottom surface of the male side of the selected region.

The primary microstructures along the longitudinal axis and/or the horizontal axis of the male side may have different types and/or densities. When the primary microstructures along the longitudinal axis of the male side of the condom (that is, from the closed end to the open end) have the same type and/or area ratio, the primary microstructures along the horizontal axis of the condom (that is, a circumference of the sleeve body equidistant to the closed end or the open end) may have different types and/or area ratios. Similarly, when the primary microstructures along the horizontal axis of the condom have the same type and/or area ratio, the primary microstructures along the longitudinal axis of the condom may have different types and/or area ratios.

It should be noted that the types and/or densities of the microstructures are distributed symmetrically along the longitudinal axis and/or horizontal axis of the sleeve body of the condom, which can be along the entire axis or only a part of a specific axis, for example, a section of the longitudinal axis ($\Delta z$ when the sleeve body of the condom serves as cylindrical polar coordinates), and a specific arc along the horizontal axis ($\Delta \varphi$ in the above cylindrical polar coordinates).

Preferably, the primary microstructure may be provided on the bottom surface of the male side at 8.0/10 to 9.8/10 of the sleeve body from the closed end, and the area ratio may be 1.1 to 50.0. Therefore, the part of the male side of the condom at 0.2/10 to 2.0/10 from the open end (for a condom with a length of 180 mm, a length of this open end part is 3.6 mm to 36 mm) is not provided with the primary microstructure. This is because this open end part does not have high requirements for slip resistance, and it is convenient to remove the condom at the end of the sexual intercourse.

Preferably, different regions of the male side on the longitudinal axis may have different average area ratios; and the closer the region to the closed end, the larger the average area ratio.

It should be noted that a section from a middle part to a glans of a penis has many nerves and needs to undergo a high exercise intensity during sexual intercourse, and thus this section should closely fit the male side of the condom; and a rear part of a penis has few nerves and only needs to undergo a low exercise intensity during sexual intercourse, and thus the rear part can fit the condom not too closely. With the above divisional design, an average area ratio of a section of the condom that contacts the section from a middle part to a glans of a penis at the male side is greater than an average area ratio of a section of the condom that contacts the rear part of a penis, such that the section of the condom from the middle to the front can closely fit with the penis skin to prevent slip and slip off and improve the reality touch, and the rear section of the condom can fit properly with a penis to facilitate the removal of the condom at the end of sexual intercourse.

Preferably, the primary microstructure may be provided on the male side at 9.0/10 of the sleeve body from the closed end; at 0/10 to 6.5/10 from the closed end, the average area ratio (S1) may be 1.2 to 20.0; at 6.5/10 to 9.0/10 (excluding 6.5/10) from the closed end, the average area ratio (S2) may be 1.1 to 5.0; and S1 may be greater than S2.

It should be noted that, with the above divisional design, the sleeve body of the condom can be further divided into many regions along the longitudinal axis and/or the horizontal axis, and different regions of the male side may be provided with primary microstructures of different types and/or densities, thereby meeting the different physiological structures and use needs of different populations.

Preferably, the primary microstructures may be distributed at the male side in different types and/or densities and in blocks and/or strips. Therefore, through the arrangement and combination of microstructured blocks and/or strips of different types and/or densities on the male side surface of the condom, an average area ratio of different regions on the male side of the condom and a fit degree of the condom with the skin can be easily adjusted to meet different needs, and there is no need to make a complicated adjustment to a production process.

Preferably, a lubricant may be attached to the condom; and preferably, the lubricant may be attached to the male side of the condom at an amount of (0.1 μg to 1.0 mg)/mm$^2$ (calculated based on a surface area of the male side, which can be the whole male side or can also be a local region of the male side). The inventors of the present disclosure find in research that when the lubricant is attached at the above amount, a gap between the sleeve body of the condom and the penis skin can be further reduced, such that the primary microstructure of the male side can well fit with the microstructure of the skin and the condom is easy to put on and take off.

Preferably, a ratio of an average height of the primary microstructure to an average outer circumference of the primary microstructure may be 157:1 to 1:16; more preferably, the ratio of the average height of the primary microstructure to the average outer circumference of the primary microstructure may be 80:1 to 1:15; and most preferably, the ratio of the average height of the primary microstructure to the average outer circumference of the primary microstructure may be 63:1 to 1:12.

Preferably, the primary microstructure may have an average height of 0.5 μm to 100 μm. More preferably, the primary microstructure may have an average height of 1.0 μm to 10.0 μm.

It should be noted that the sizes and/or geometric shapes of the primary microstructures of the male side in the present disclosure may be different in the height and/or outer circumference, which may be for the same primary microstructure and/or different primary microstructures. The average height refers to an average height value of all microstructures of different heights and/or shapes in a given male side region, and the average outer circumference refers to an average outer circumference value of all microstructures in a given male side region (when the primary microstructures have different thicknesses and/or properties and/or have a secondary microstructure, it is necessary to obtain an average outer circumference of each primary microstructure and then obtain an average outer circumference of all microstructures).

Preferably, the primary microstructures may be arranged on the bottom surface of the male side at a density of 0.31 to $10^{10}$ microstructures/mm$^2$. More preferably, the density may be $10^2$ to $10^8$ microstructures/mm$^2$. Most preferably, the density may be $10^4$ to $2.5\times10^7$ microstructures/mm$^2$. It should be noted that, since an absolutely-uniform density distribution cannot be obtained through any process, the density in the present disclosure actually refers to an average number of all primary microstructures in a given male side region. By adjusting the average height and density of the primary microstructures within a required range, the area ratio can be adjusted from one to hundreds.

Preferably, the primary microstructure may have a secondary microstructure, and the secondary microstructure may also have a tertiary microstructure. The introduction of the secondary or tertiary microstructures can further increase the area ratio of the male side, make the microstructure of the male side well fit with the microstructure of the penis skin complementarily, and can further improve the reality touch, especially in parts with the densest nerve distribution, such as glans and coronal sulcus.

Preferably, an average height of the secondary microstructure may be 1/2 to 1/100 of the average height of the primary microstructure.

Preferably, the primary microstructure and/or the secondary microstructure may be at least one from the group consisting of a column structure, a sawtooth structure, and a bump structure. Therefore, the primary microstructures and/or the secondary microstructures may be composed of at least one from the above-mentioned different microstructures, and an area ratio difference among different regions of the male side of the condom can be achieved through the adjacent juxtaposition and/or regional arrangement of the three different microstructures. In the adjacent juxtaposition, two adjacent microstructures are different (the two microstructures can be directly connected and can also be separated by a smooth bottom region); and in the regional arrangement, microstructures in each small region are the same, but microstructures in adjacent regions may be different (two small regions can be directly connected and can also be separated by a smooth bottom region). It should be noted that the above-mentioned various structures (including the column structure, the sawtooth structure, and the bump structure) cannot be absolutely-symmetrical simple geometric structures in reality. Therefore, for the measurement of various dimensions of the structures, necessary approximation processing, indirect measurement and/or calculation, extension processing (such as angle), and averaging processing (such as uneven surfaces or lines) are required.

Preferably, the primary microstructure and/or the secondary microstructure may be a column structure, and the column structure may be at least one from the group consisting of a rotator and a column.

Preferably, a ratio of an average height to an average outer circumference of the column structure may be 157:1 to 4:1; the column structure may have an average height of 0.5 μm to 100 μm; and the column structure may be arranged at a density of 0.31 to $10^{10}$ structures/mm$^2$.

Preferably, the primary microstructure and/or the secondary microstructure may be a sawtooth structure.

Preferably, the sawtooth structure may have an average height of 0.5 μm to 5.0 μm; in the sawtooth structure, an average included angle of tops of saw teeth in a cross section in any direction may not exceed 160°; and the sawtooth structure may be arranged at a density of 164 to $10^{10}$ structures/mm$^2$.

It should be noted that the sawtooth structure refers to a three-dimensional (3D) structure with a wide bottom and a narrow or even sharp top; and a specified longitudinal section of these 3D structures can be a triangular shape, a trapezoidal shape, or an approximate shape, and these shapes may be or may not be horizontally and/or longitudinally symmetrical. The bump structure may be a microstructure that can well attach to, hook, and fit with the skin surface, including a micro-hook structure.

Preferably, the primary microstructure and/or the secondary microstructure may be a bump structure.

Preferably, the bump structure may have an average height of 0.5 μm to 5.0 μm, and the bump structure may be arranged at a density of 636 to $10^{10}$ structures/mm$^2$.

It should be noted that, the bump structure refers to a 3D structure with a top that is not sharp and has a width close to the width of a bottom, which has an average height similar to the average height of the sawtooth structure; and a specified longitudinal section of these 3D structures can be a rectangular shape, a parabolic shape, a semicircular shape, an arc shape, or an approximate shape, and these shapes may be or may not be horizontally and/or longitudinally symmetrical.

The condom of the present disclosure can be made of rubber latex, polyurethane (PU), graphene, or other materials.

In summary, the present disclosure has the following beneficial effects.

The present disclosure provides a non-slip condom, where at least 5% of a bottom surface of a male side is provided with a primary microstructure, and an area ratio of a total surface area per unit area of the bottom surface of the male side including the primary microstructure to the unit area is 1.05 to 565.00. This condom can increase a surface area of the male side, improve the effective contact area between the condom and the penis skin, prevent the relative slip between the condom and the penis skin, and can also be easily removed after use. The condom is not easy to wrinkle or slip off in use, thus reducing the mucosal injury and unreality sensation. Moreover, the condom helps to increase the consumers' willingness to use the condom and prevent STDs.

BRIEF DESCRIPTION OF THE DRAWINGS

FIG. 2 and FIG. 3 are images of a skin surface under a microscope;

FIG. 4A is a schematic enlarged partial view of a male side with a primary cylindrical microstructure, and FIG. 4B is a schematic 3D structural diagram of an enlarged part of FIG. 4A;

FIG. 5A is a schematic enlarged partial view of a male side with a regular primary sawtooth microstructure, and FIG. 5B is a schematic 3D structural diagram of an enlarged part of FIG. 5A;

FIG. 6A is a schematic enlarged partial view of a male side with an irregular primary sawtooth microstructure, and FIG. 6B is a schematic 3D structural diagram of an enlarged part of FIG. 6A;

FIG. 7A is a schematic enlarged partial view of a male side with a bump primary microstructure, and FIG. 7B is a schematic 3D structural diagram of an enlarged part of FIG. 7A;

FIG. 8A is a schematic enlarged partial view of a male side with a primary cylindrical microstructure and a secondary cylindrical microstructure, and FIG. 8B is a schematic 3D diagram of an enlarged part of FIG. 8A;

REFERENCE NUMERALS

Figure 1:
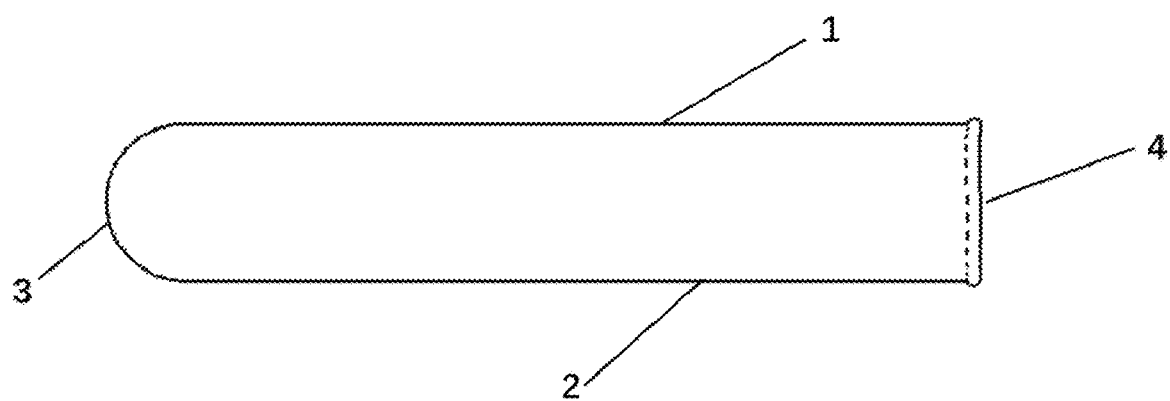
FIG. 1 is a schematic diagram of a structure of the condom.
Figure 2:
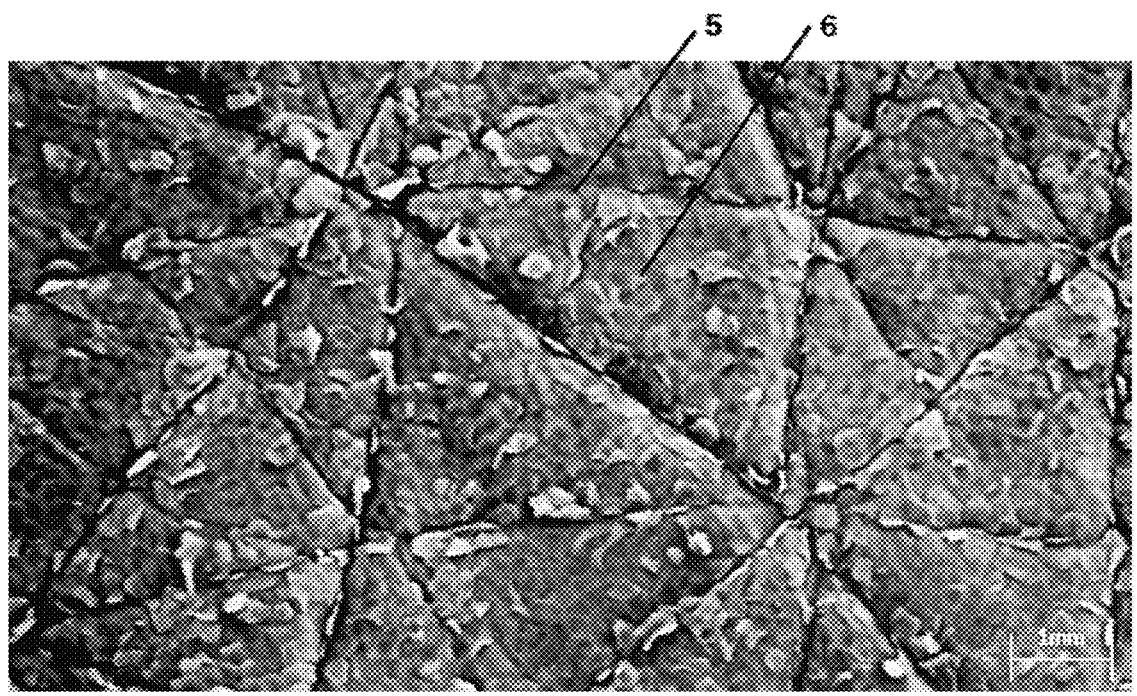

1: male side; 2: female side; 3: closed end; 4: open end; 5: skin groove; 6: skin bulge; 7: uneven microstructure on skin; 8: primary cylindrical microstructure; 9: regular primary sawtooth microstructure; 10: irregular primary sawtooth microstructure; 11: primary bump microstructure; 12: secondary cylindrical microstructure; and 13: primary microstructure distributed in block or strip.

DETAILED DESCRIPTION

Some names, test methods, and test materials involved in the present disclosure are briefly described below:

Male Side

In the examples of the present disclosure, unless otherwise specified, the surface, surface area, and area ratio refer to the characteristics of the male side of the sleeve body of the condom in contact with a penis.

Surface Area

The surface area used in the examples of the present disclosure is obtained through conventional measurement and integral calculation according to a structural dimension of the surface of the condom.

Area Ratio

The area ratio used in the examples of the present disclosure is obtained by dividing a surface area of a selected region of the male side of the condom with a bottom surface area of the selected region, where the bottom surface is an imaginary smooth surface.

Slip Force Determination

The effective contact area is positively correlated with the slip force. The larger the effective contact area, the larger the slip force. Therefore, the slip force is used to characterize the effective contact area.

The condom is sleeved on a cylinder with a diameter of 34 mm, a surface of the cylinder is made of artificial leather whose surface structure and softness are similar to human skin, and a length of the condom wrapping the cylinder is 180 mm. A top of the condom is clamped, then the condom is subjected to a tensile test on a tensile analyzer at a tensile speed of 500 mm/min, and a force value causing a significant slip between the condom and the cylinder is recorded.

Condom Sample

The condom used in the examples of the present disclosure is a male condom made of natural rubber latex. The condom has a thickness of 50 μm and a length of 180 mm.

To better explain the objectives, technical solutions, and advantages of the present disclosure, the present disclosure will be further explained below with reference to accompanying drawings and specific examples. Unless otherwise specified, the parameter values used in the present disclosure are average values of multiple groups or times.

Example 1

In an example of the condom of the present disclosure, all regions of the male side of the condom have primary cylindrical microstructures 8 that are uniformly arranged, as shown in FIG. 4. h represents a height of the cylinder microstructure, d represents a diameter of a single cylinder microstructure, and l represents an average circumference of a single cylinder microstructure. Table 1 shows an area ratio of the male side of the condom calculated according to the structural parameters of the cylinder structure.

TABLE 1

Area ratios when all regions of the male side have the primary cylindrical microstructure

| Condom Type/No. | Height h /μm | Diameter d/μm | Circumference l/μm | Arrangement density $10^4$ structures/ $mm^2$ | Area ratio |
|---|---|---|---|---|---|
| Z-0 (ordinary smooth surface) | / | / | | / | 1 |
| A-1 | 10 | 2 | 6.3 | 0.4 | 1.25 |
| A-2 | 6 | 2 | 6.3 | 2.7 | 2.02 |
| A-3 | 50 | 2 | 6.3 | 6.4 | 21.11 |
| A-4 | 100 | 1.5 | 4.71 | 10 | 48.12 |
| A-5 | 100 | 0.75 | 2.36 | 40 | 95.25 |
| A-6 | 100 | 0.5 | 1.57 | 100 | 158.08 |
| A-7 | 100 | 0.5 | 1.57 | 360 | 566.49 |

Example 2

In an example of the condom of the present disclosure, all regions of the male side of the condom have regular primary sawtooth microstructures 9 that are closely arranged, as shown in FIG. 5. The sawtooth structure is a regular square pyramid; and h represents a height of a single saw tooth, w represents a side length of a bottom of a single saw tooth, and a is an apex angle of a sawtooth cone. Table 2 shows an area ratio of the male side calculated according to the structural parameters of the sawtooth microstructure.

TABLE 2

Area ratios when all regions of the male side have the regular primary sawtooth microstructure

| Condom Type/No. | Height h/μm | Bottom side length w/μm | Apex angle α/° | Area ratio |
|---|---|---|---|---|
| Z-0 (ordinary smooth surface) | / | / | / | 1 |

TABLE 2-continued

Area ratios when all regions of the male side have the regular primary sawtooth microstructure

| Condom Type/No. | Height h/μm | Bottom side length w/μm | Apex angle α/° | Area ratio |
|---|---|---|---|---|
| B-1 | 0.5 | 1 | 70.53 | 1.41 |
| B-2 | 5 | 1 | 11.36 | 10.05 |
| B-3 | 5 | 0.5 | 5.72 | 20.03 |
| B-4 | 25 | 0.5 | 1.15 | 50.01 |

Example 3

In an example of the condom of the present disclosure, all regions of the male side of the condom have irregular primary sawtooth microstructures 10 that are closely arranged, as shown in FIG. 6. Structural parameters of the irregular sawtooth microstructure are expressed as average values, including: an average spacing L of saw teeth and an average height H of saw teeth.

The average spacing L of saw teeth and the average height H of saw teeth include values in two directions a and b that are orthogonal to each other on a test plane, which are denoted as $L_a$, $L_b$, $H_a$, and $H_b$, respectively.

With the infinitesimal method, a surface area of the male side with the irregular sawtooth microstructure is regarded as an area integral of an infinitesimal plane in the two directions of a and b. The area ratio of the male side is calculated by the following formula, and results obtained are shown in Table 3.

$$\text{Area ratio} = \frac{\sqrt{(4H_a^2 + L_a^2) \times (4H_b^2 + L_b^2)}}{L_a \times L_b}$$

TABLE 3

Area ratios when all regions of the male side have the irregular primary sawtooth microstructure

| Condom Type/No. | $L_a$ /μm | $H_a$ /μm | $L_b$ /μm | $H_b$ /μm | Area ratio |
|---|---|---|---|---|---|
| Z-0 (ordinary smooth surface) | / | / | / | / | 1 |
| C-1 | 89 | 6.9 | 91 | 7.3 | 1.025 |
| C-2 | 79.1 | 10.9 | 81.5 | 10.6 | 1.072 |
| C-3 | 63.4 | 11.3 | 72.9 | 12.1 | 1.119 |
| C-4 | 54.2 | 25.1 | 53.7 | 23.9 | 1.825 |
| C-5 | 43.2 | 53.4 | 46.6 | 59.7 | 7.335 |
| C-6 | 32.4 | 56.7 | 33.9 | 55.1 | 12.380 |
| C-7 | 26.4 | 89.1 | 27.1 | 85.4 | 43.545 |

Example 4

In an example of the condom of the present disclosure, all regions of the male side of the condom have primary bump microstructures 11 that are closely arranged, as shown in FIG. 7. h represents a height of the bump microstructure, d represents a diameter of a single bump microstructure, and l represents a circumference of a single bump microstructure. Table 4 shows an area ratio of the male side of the condom calculated according to the structural parameters of the bump structure.

TABLE 4

Area ratios when all regions of the male side have the primary bump microstructure

| Condom Type/No. | Height h/μm | Diameter d/μm | Circumference l/μm | Bump arrangement density $10^4$ structures/mm² | Area ratio |
|---|---|---|---|---|---|
| Z-0 (ordinary smooth surface) | / | / | / | / | 1 |
| D-0 (regular floating point) | 500 | 500 | 1570.8 | 0.000004 | 1.031 |
| D-1 | 5 | 1.5 | 4.7 | 10 | 3.356 |
| D-2 | 5 | 0.5 | 1.6 | 90 | 8.069 |
| D-3 | 3 | 1 | 3.1 | 20 | 2.885 |
| D-4 | 3 | 0.8 | 2.5 | 20 | 2.508 |
| D-5 | 5 | 0.8 | 2.5 | 40 | 6.027 |

Example 5

In an example of the condom of the present disclosure, all regions of the male side of the condom have primary cylindrical microstructures 8 that are uniformly arranged, and the primary cylindrical microstructures 8 have secondary cylindrical microstructures 12 with a smaller size than the primary cylindrical microstructures, where each primary cylindrical microstructure has 4 secondary cylindrical microstructures, as shown in FIG. 8. $h_1$ and $d_1$ represent a height and a diameter of a single primary cylindrical microstructure, respectively; $h_2$ and $d_2$ represent a height and a diameter of a single secondary cylindrical microstructure, respectively; and the primary cylindrical microstructures are arranged on the bottom surface of the male side at a density of 80,000 structures/mm². Table 5 shows an area ratio of the male side calculated according to the structural parameters of the primary and secondary microstructures.

TABLE 5

Area ratios when all regions of the male side of the condom have the primary and secondary cylindrical microstructures

| Condom Type/No. | Primary structure Height $h_1/\mu m$ | Primary structure Diameter $d_1/\mu m$ | Secondary structure Height $h_2/\mu m$ | Secondary structure Diameter $d_2/\mu m$ | Area ratio |
|---|---|---|---|---|---|
| E-1 | 10 | 2 | 2 | 0.5 | 8.54 |
| E-2 | 10 | 2 | 2 | 0.3 | 7.54 |
| E-3 | 6 | 2 | 2 | 0.5 | 6.53 |
| E-4 | 6 | 2 | 2 | 0.3 | 5.52 |
| E-5 | 50 | 2 | 5 | 0.5 | 32.4 |
| E-6 | 50 | 2 | 5 | 0.3 | 29.90 |
| E-7 | 100 | 1.5 | 10 | 0.3 | 46.24 |

Example 6

In an example of the condom of the present disclosure, the entire surface of the male side has primary cylindrical microstructures that are closely arranged, and the primary cylindrical microstructures have secondary cylindrical microstructures. Parameters for the primary microstructures: height: 10 single microstructure diameter: 5 and density: 10,000 structures/mm². A single secondary cylindrical microstructure on each primary cylindrical microstructure has a height of 5 μm and a diameter of 0.5 μm; and in each primary cylinder structure for different samples, there may be 0, 10, 25, and 50 secondary cylinder structures. Table 6 shows a relative area ratio growth factor of the male side where all regions have the primary and secondary microstructures compared with the male side where all regions only have the primary microstructure and do not have the secondary microstructure.

TABLE 6

Relative area ratio growth factors of the male side with the primary and secondary microstructures compared with the male side only with the primary microstructure.

| Condom Type/No. | Number of secondary microstructures | Area ratio | Relative area ratio growth factor |
|---|---|---|---|
| F-0 (without secondary microstructure) | 0 | 16.708 | 1 |
| F-1 | 10 | 17.493 | 1.047 |
| F-2 | 25 | 18.671 | 1.117 |
| F-3 | 50 | 20.635 | 1.235 |

Example 7

In an example of the condom of the present disclosure, the male side of the condom is provided with discrete block microstructures, where the primary microstructures have an area ratio of 1.25. The microstructures with an area ratio of 1.25 are distributed on the male side in discrete blocks with proportions of 0%, 5%, 10%, 20%, 50%, 75%, and 100% to obtain samples G-1, G-2, G3, G4, G5, and G6, respectively.

200 mg of a water-soluble lubricant is uniformly coated on the male side, a slip force is measured for each condom sample, and results are shown in Table 7.

TABLE 7

Average area ratio and slip force F (N) of the male side provided with primary microstructures with the same area ratio in different proportions

| Condom Type/No. | Proportion of primary microstructures on male side/% | Average area ratio of male side | Slip force F (N) |
|---|---|---|---|
| Z-0 | 0 | 1 | 62.13 |
| G-1 | 5 | 1.0125 | 67.09 |
| G-2 | 10 | 1.025 | 72.01 |
| G-3 | 20 | 1.05 | 87.38 |
| G-4 | 50 | 1.125 | 110.09 |
| G-5 | 75 | 1.1875 | 134.31 |
| G-6 | 100 | 1.25 | 152.95 |

Above results show that, the larger the proportion of a part with the primary microstructure in the entire male side of the condom, the higher the average area ratio of the male side and the closer the average area ratio of the male side to the area ratio of the primary microstructure itself; and the larger the slip force of the condom, the greater the effective contact area.

Example 8

Figure 9:
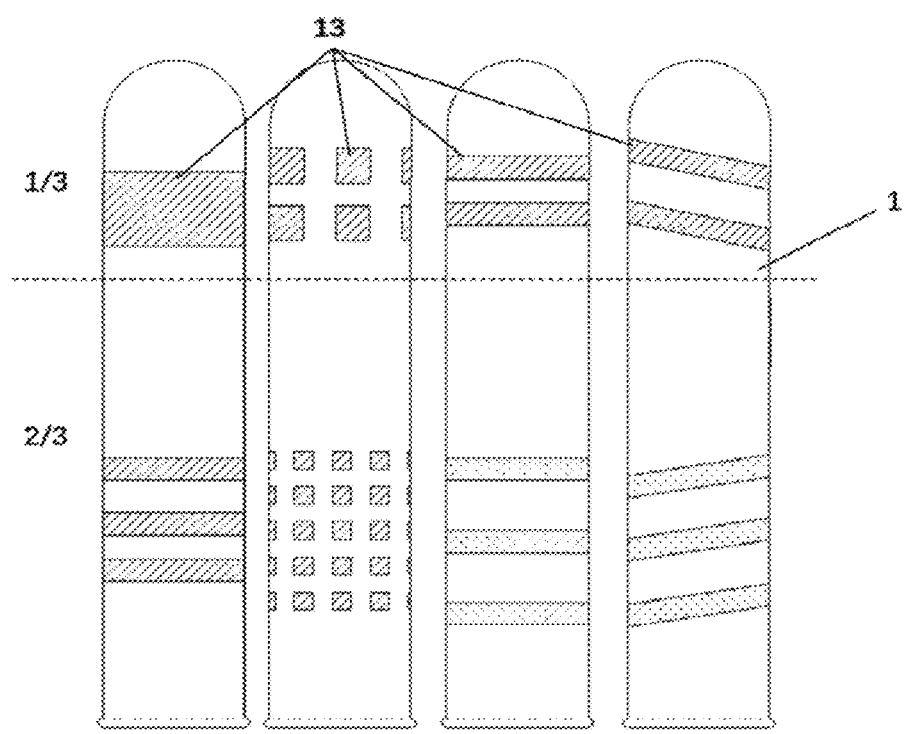
FIG. 9 is a cross-sectional view of an example of the condom of the present disclosure, where a male side of the condom is provided with primary microstructures distributed in blocks or strips.

In an example of the condom of the present disclosure, primary microstructures with different area ratios are arranged on the male side of the condom in blocks and strips at an interval, as shown in FIG. 9. $S_n$ (n=1, 2, 3 . . . ) represents an area ratio of a region where primary microstructures 13 are distributed in blocks or stripes, $\overline{S}_{mo}$ represents an average area ratio of a region at 1/3 from the closed end of the male side of the condom, and $\overline{S}_{mc}$ represents an average area ratio of a region at 2/3 from the open end of the male side of the condom. Slip forces of condom samples where a lubricant is attached to the male side at different contents are measured, and results are shown in Table 8.

TABLE 8

Slip forces F of condom samples where primary microstructures are distributed in blocks and strips on the male side and a water-soluble lubricant is attached at different contents (N)

| Condom Type/No. | Average area ratio | | Water-soluble lubricant content (mg/mm²) | | | | | |
|---|---|---|---|---|---|---|---|---|
| | $\overline{S}_{mo}$ | $\overline{S}_{mc}$ | 0 | 0.2 | 0.4 | 0.6 | 0.8 | 1 |
| Z-0 | 1 | | 61.12 | 60.73 | 62.45 | 61.10 | 63.20 | 61.70 |
| C-1 | 1.03 | | 62.31 | 63.07 | 61.02 | 64.32 | 63.12 | 61.77 |
| D-0 | 1.03 | | 61.08 | 62.39 | 63.20 | 61.89 | 63.54 | 62.78 |
| H-1 | 1.25 | 1.41 | 62.20 | 86.96 | 76.54 | 75.93 | 74.85 | 73.30 |
| H-2 | 1.25 | 6.03 | 89.73 | 233.87 | 121.39 | 118.22 | 120.96 | 122.33 |
| H-3 | 2.89 | 6.03 | 108.15 | 259.78 | 325.15 | 159.78 | 157.52 | 149.17 |

TABLE 8-continued

Slip forces F of condom samples where primary microstructures
are distributed in blocks and strips on the male side and a
water-soluble lubricant is attached at different contents (N)

| Condom Type/No. | Average area ratio $\overline{S}_{mo}$ | $\overline{S}_{mc}$ | Water-soluble lubricant content (mg/mm$^2$) 0 | 0.2 | 0.4 | 0.6 | 0.8 | 1 |
|---|---|---|---|---|---|---|---|---|
| H-4 | 2.89 | 12.38 | 128.14 | 286.20 | 354.35 | 417.66 | 389.66 | 340.33 |
| H-5 | 3.36 | 12.38 | 138.93 | 301.83 | 364.79 | 392.93 | 485.69 | 348.02 |
| H-6 | 3.36 | 20.03 | 209.24 | 275.08 | 325.63 | 465.90 | 498.10 | 563.35 |

Test results show that, at different water-soluble lubricant contents, the slip force increases as the average area ratio increases; and especially when the average area ratio of the region at 2/3 from the open end of the male side of the condom increases, the slip force increases significantly.

Example 9

The effects of the condoms of the present disclosure were verified in this example. Some condom samples were selected from Examples 1 to 8, and a water-soluble lubricant was uniformly coated on the male side of a selected sample at an amount of 400 mg/mm$^2$.

Ten volunteers were selected for a personal experience test. Each subject was allocated with 2 condoms of each type that were coated with a lubricant, and filled out a subjective evaluation effect visit form after use. Forms of all volunteers were collected for statistics, and results were shown in Table 9.

TABLE 9

Subjective experience evaluation of the volunteers for the condoms

| Type/No. | Reality sensation | No slip | Easy removal | Wrinkle or slip off |
|---|---|---|---|---|
| Z-0 | 3 | 3 | 10 | 3 |
| D-0 | 2 | 3 | 10 | 3 |
| A-1 | 9 | 9 | 10 | 9 |
| A-2 | 9 | 9 | 10 | 9 |
| A-3 | 10 | 10 | 8 | 10 |
| A-4 | 10 | 10 | 8 | 10 |
| B-1 | 9 | 9 | 10 | 9 |
| B-2 | 10 | 10 | 10 | 10 |
| B-3 | 10 | 10 | 9 | 10 |
| B-4 | 10 | 10 | 8 | 10 |
| C-1 | 7 | 8 | 10 | 8 |
| C-5 | 10 | 10 | 10 | 10 |
| C-7 | 10 | 10 | 7 | 10 |
| D-1 | 10 | 10 | 10 | 10 |
| D-2 | 10 | 10 | 10 | 10 |
| D-4 | 10 | 10 | 10 | 10 |
| E-1 | 9 | 9 | 10 | 9 |
| E-7 | 10 | 10 | 10 | 10 |
| F-1 | 10 | 10 | 9 | 10 |
| F-2 | 10 | 10 | 9 | 10 |
| G-2 | 9 | 9 | 10 | 9 |
| G-4 | 9 | 9 | 10 | 8 |
| G-5 | 9 | 9 | 10 | 9 |
| H-1 | 9 | 9 | 10 | 10 |
| H-2 | 9 | 9 | 10 | 10 |
| H-3 | 10 | 10 | 10 | 10 |
| H-4 | 10 | 10 | 10 | 10 |
| H-5 | 10 | 10 | 10 | 10 |
| H-6 | 10 | 10 | 10 | 10 |

Notes:
The evaluation is conducted based on 0 to 10 scores, where 10 is a full score, and a score is expressed by an integer.
Reality sensation: The closer the subjective sensation to the sensation when no condom is worn, the higher the score.
No slip: It is observed whether the condom slips during sexual intercourse. When the condom does not slip at all, a score of 10 is given.
Easy removal: It is observed whether the condom is easy to remove at the end of sexual intercourse. The easier the condom is to remove, the higher the score. Wrinkle or slip off: If the condom slips off, a score of 0 is given; a corresponding score is given according to a wrinkle degree; and if there is no wrinkle at all, a score of 10 is given.

Example 10

A condom of the present disclosure is provided, where 5% of the bottom surface of the male side is provided with a primary microstructure capable of increasing a surface area, a region with the primary microstructure has an area ratio of 1.05, and a lubricant is attached to the male side of the condom at an amount of 5×10$^{-3}$ mg/mm$^2$, which is denoted as sample 1.

Example 11

A condom of the present disclosure is provided, where 20% of the bottom surface of the male side is provided with a primary microstructure capable of increasing a surface area, a region with the primary microstructure has an area ratio of 500, and a lubricant is attached to the male side of the condom at an amount of 5×10$^{-3}$ mg/mm$^2$, which is denoted as sample 2.

Example 12

A condom of the present disclosure is provided, where 95% of the bottom surface of the male side is provided with a primary microstructure capable of increasing a surface area, a region with the primary microstructure has an area ratio of 1.2, and a lubricant is attached to the male side of the condom at an amount of 5×10$^{-3}$ mg/mm$^2$, which is denoted as sample 3. The primary microstructure is a bump structure with an average height of 1,000 nm.

Example 13

A condom of the present disclosure is provided, where 95% of the bottom surface of the male side is provided with a primary microstructure capable of increasing a surface area, a region with the primary microstructure has an area ratio of 100, and a lubricant is attached to the male side of the condom at an amount of $10 \times 10^{-3}$ mg/mm$^2$, which is denoted as sample 4. The primary microstructure is a column structure with a height of 5,000 nm.

Example 14

A condom of the present disclosure is provided, where regions of the male side at 9/10 from the closed end to the open end are provided with a primary microstructure and have an area ratio of 50, regions at 6.5/10 from the closed end to the open end have an average area ratio (S1) of 20, and regions at 6.5/10 to 9/10 (excluding 6.5/10) have an average area ratio (S2) of 1.1; and a lubricant is attached to the male side of the condom at an amount of $20 \times 10^{-3}$ mg/mm$^2$, which is denoted as sample 5. The primary microstructure is a sawtooth structure with an average height of 2,000 nm, and an included angle of tops of saw teeth in the sawtooth structure is 30° to 140°.

Example 15

A condom of the present disclosure is provided, where regions of the male side at 9/10 from the closed end to the open end are provided with a primary microstructure and have an area ratio of 200, and other regions are not provided with a microstructure; regions at 6.5/10 from the closed end to the open end have an average area ratio (S1) of 15, and regions at 6.5/10 to 9/10 (excluding 6.5/10) have an average area ratio (S2) of 3; and a lubricant is attached to the male side of the condom at an amount of $20 \times 10^{-3}$ mg/mm$^2$, which is denoted as sample 6. The primary microstructure is a sawtooth structure.

Example 16

A condom of the present disclosure is provided, where 40% of the bottom surface of the male side is provided with a primary microstructure capable of increasing a surface area, and a region provided with the primary microstructure has an area ratio of 250; the primary microstructure has an average height of 1,500 nm, there is also a secondary microstructure on the primary microstructure, and the secondary microstructure has a height of 600 nm; and a lubricant is attached to the male side of the condom at an amount of $20 \times 10^{-3}$ mg/mm$^2$, which is denoted as sample 7.

Example 17

This example is different from Example 12 in that there is a secondary microstructure on the primary microstructure, and the secondary microstructure has a height of 600 nm; and the sample is denoted as sample 8.

Example 18

This example is different from Example 13 in that there is a secondary microstructure on the primary microstructure, and the secondary microstructure has a height of 500 nm; and the sample is denoted as sample 9.

Example 19

This example is different from Example 15 in that S2 is 5, and the sample is denoted as sample 10.

Example 20

This example is different from Example 13 in that there is a secondary microstructure on the primary microstructure, and the secondary microstructure has a height of 1,200 nm; and the sample is denoted as sample 11.

Example 21

The samples of Examples 10 to 20 of the present disclosure and a control sample were subjected to a personal experience test on 10 volunteers. The control sample was a common condom (where a lubricant is attached to the male side at an amount of $25 \times 10^{-3}$ mg/mm$^2$) without any microstructure (area ratio of 1). Each subject was allocated with 2 condoms of each type, and filled out a subjective evaluation visit form after use. Forms of all subjects were collected for statistics, and results were shown in Table 10.

TABLE 10

Summary of subjective evaluation results of the volunteers

| Test sample | Area ratio of the region with the microstructure | Reality sensation | No slip | Easy removal | Wrinkle or Slip off |
|---|---|---|---|---|---|
| Sample 1 | 1.1 | 9 | 9 | 10 | 9 |
| Sample 2 | 500.0 | 10 | 10 | 6 | 10 |
| Sample 3 | 1.2 | 10 | 10 | 10 | 10 |
| Sample 4 | 100.0 | 10 | 10 | 7 | 10 |
| Sample 5 | 50.0 | 10 | 10 | 10 | 10 |
| Sample 6 | 200.0 | 10 | 10 | 10 | 10 |
| Sample 7 | 250.0 | 9 | 9 | 8 | 9 |
| Sample 8 | 1.2 | 10 | 10 | 10 | 10 |
| Sample 9 | 100.0 | 10 | 10 | 7 | 10 |
| Sample 10 | 50.0 | 10 | 10 | 10 | 10 |
| Sample 11 | 100.0 | 10 | 10 | 7 | 10 |
| Control Z-0 | 1.0 | 3 | 3 | 10 | 3 |

Note:
The scoring criteria and content are the same as Table 9.

Experimental results of Example 9 and Example 21 show that the condom of the present disclosure (where no less than 5% of the bottom surface of the male side is provided with a primary microstructure capable of increasing a surface area and an area ratio of a total surface area per unit area of the bottom surface of the male side including the primary microstructure to the unit area is 1.05 to 565.00) leads to high reality sensation, is not easy to slip and wrinkle or slip off, and shows a sensory experience effect significantly higher than that of the control sample.

Results of Example 9 and Example 21 also show that, with the divisional design for the male side, regions at 0/10 to 6.5/10 from the closed end to the open end have an average area ratio (S1) of 1.2 to 50.0, regions at 6.5/10 to 9.0/10 (excluding 6.5/10) from the closed end to the open end have an average area ratio (S2) of 1.05 to 10.0, and S1 is greater than S2, which can effectively reduce the slip of the condom during sexual intercourse and allows the condom to be easily removed after sexual intercourse, thereby providing a prominent use experience.

Finally, it should be noted that the above examples are provided merely to describe the technical solutions of the present disclosure, rather than to limit the protection scope of the present disclosure. Although the present disclosure is described in detail with reference to preferred examples, a person of ordinary skill in the art should understand that modifications or equivalent replacements may be made to the technical solutions of the present disclosure without departing from the spirit and scope of the technical solutions of the present disclosure.

The invention claimed is:

1. A condom, comprising a sleeve body, wherein the sleeve body has an open end, a closed end, a male side, and a female side; no less than 5% of a bottom surface of the male side has a primary microstructure capable of increasing a surface area; and an area ratio of a total surface area per unit area of the bottom surface of the male side comprising the primary microstructure to the unit area is 1.05 to 565.00.

2. The condom according to claim 1, wherein a ratio of an average height of the primary microstructure to an average outer circumference of the primary microstructure is 157:1 to 1:16.

3. The condom according to claim 2, wherein there is a secondary microstructure on the primary microstructure.

4. The condom according to claim 3, wherein the primary microstructure and/or the secondary microstructure are/is at least one from the group consisting of a column structure, a sawtooth structure, and a bump structure.

5. The condom according to claim 4, wherein the column structure is at least one from the group consisting of a rotator and a column.

6. The condom according to claim 5, wherein a ratio of an average height to an average outer circumference of the column structure is 157:1 to 4:1; the column structure has an average height of 0.5 μm to 100 μm; and the column structure is arranged at a density of 0.31 to $10^{10}$ structures/mm².

7. The condom according to claim 4, wherein the sawtooth structure has an average height of 0.5 μm to 5 μm; in the sawtooth structure, an average included angle of tops of saw teeth in a cross section in any direction does not exceed 160°; and the sawtooth structure is arranged at a density of 164 to $10^{10}$ structures/mm².

8. The condom according to claim 4, wherein the bump structure has an average height of 0.5 μm to 5 μm, and the bump structure is arranged at a density of 636 to $10^6$ structures/mm².

9. The condom according to claim 3, wherein an average height of the secondary microstructure is 1/2 to 1/100 of the average height of the primary microstructure.

10. The condom according to claim 1, wherein the primary microstructure is provided on the bottom surface of the male side at 8.0/10 to 9.8/10 of the sleeve body from the closed end, and the area ratio is 1.1 to 50.0.

11. The condom according to claim 10, wherein the primary microstructure is provided on the bottom surface of the male side at 9.0/10 of the sleeve body from the closed end; at 0/10 to 6.5/10 from the closed end, the average area ratio (S1) is 1.2 to 20.0; at 6.5/10 to 9.0/10 (excluding 6.5/10) from the closed end, the average area ratio (S2) is 1.1 to 5.0; and S1 is greater than S2.

12. The condom according to claim 10, wherein the primary microstructures are distributed at the male side in different types and/or quantities and in blocks and/or strips.

13. The condom according to claim 1, wherein a lubricant is attached to the condom.

14. The condom according to claim 13, wherein the lubricant is attached to the male side of the condom at an amount of (0.1 μg to 1.0 mg)/mm² (calculated based on a surface area of the male side).

15. The condom according to claim 1, wherein the primary microstructure has an average height of 0.5 μm to 100 μm.

16. The condom according to claim 15, wherein the primary microstructure has an average height of 1 μm to 10 μm.

17. The condom according to claim 1, wherein the primary microstructures are arranged on the bottom surface of the male side at a density of 0.31 to $10^{10}$ microstructures/mm².

18. The condom according to claim 17, wherein the density is $10^2$ to $10^8$ microstructures/mm².

19. The condom according to claim 1, wherein 20% to 95% of the bottom surface of the male side has the primary microstructure capable of increasing a surface area.

20. The condom according to claim 1, wherein the area ratio is 1.1 to 100.0.

21. The condom according to claim 1, wherein different regions with the primary microstructure on a longitudinal axis and/or a horizontal axis of the male side have the same average area ratio.

22. The condom according to claim 1, wherein different regions of the surface of the male side on a longitudinal axis have different average area ratios, and the closer the region to the closed end, the larger the average area ratio.

* * * * *